(12) United States Patent
Marion et al.

(10) Patent No.: US 9,193,676 B2
(45) Date of Patent: *Nov. 24, 2015

(54) METHOD FOR PRODUCING COMPOUNDS COMPRISING NITRILE FUNCTIONS

(71) Applicant: RHODIA OPERATIONS, Aubervilliers (FR)

(72) Inventors: Phillppe Marion, Vernaison (FR); Roland Jacquot, Francheville (FR); Laurence Grimaud, Paris (FR); Damien Cartigny, La Rochelle (FR); Laurent Elkaim, Paris (FR)

(73) Assignee: RHODIA OPERATIONS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,366

(22) PCT Filed: Nov. 16, 2012

(86) PCT No.: PCT/EP2012/072849
§ 371 (c)(1),
(2) Date: May 15, 2014

(87) PCT Pub. No.: WO2013/072466
PCT Pub. Date: May 23, 2013

(65) Prior Publication Data
US 2014/0350265 A1    Nov. 27, 2014

(30) Foreign Application Priority Data
Nov. 18, 2011  (FR) ...................................... 11 60534

(51) Int. Cl.
*C07C 69/34* (2006.01)
*C07C 255/00* (2006.01)
*C07C 253/30* (2006.01)
*C07D 211/88* (2006.01)
*C07C 253/00* (2006.01)
*C07D 211/02* (2006.01)

(52) U.S. Cl.
CPC ............. *C07C 253/30* (2013.01); *C07C 253/00* (2013.01); *C07D 211/02* (2013.01); *C07D 211/88* (2013.01); *C07C 2101/14* (2013.01)

(58) Field of Classification Search
CPC ...................................................... C07C 253/00
USPC ........................................... 560/190; 558/378
See application file for complete search history.

(56) References Cited

FOREIGN PATENT DOCUMENTS

FR      2922887 A1     1/2009
WO    2011144619 A1   11/2011

OTHER PUBLICATIONS

Klein, J .Org. Chem., vol. 36, No. 20, 1971, 3050-3051.*
Klein, J. Org. Chem, vol. 36, No. 20, 1971, 3050-3051.
Laeckmann D. et al., Bioorganic & Medicinal Chemistry, Pergamon, vol. 10, No. 6, 2002, 1793-1804.

* cited by examiner

*Primary Examiner* — Nizal Chandrakumar

(57) ABSTRACT

The present invention concerns the production of compounds comprising nitrite functions and cyclic imide compounds. More specifically, the invention relates to the production of compounds comprising nitrile functions from compounds comprising carboxylic functions, advantageously of natural and renewable origin, and from methyl-2 glutaronitrile (MGN) or a mixture N of dinitriles comprising methyl-2 glutaronitrile (MGN), ethyl-2 succinonitrile (ESN) and adiponitrile (AdN).

10 Claims, No Drawings

METHOD FOR PRODUCING COMPOUNDS COMPRISING NITRILE FUNCTIONS

This application is a U.S. national stage entry under 35 U.S.C. §371 of International Application No. PCT/EP2012/072849, filed Nov. 16, 2012, which claims priority to French Application No. 1160534 filed on Nov. 18, 2011. The entire content of each of these applications is hereby incorporated herein.

The present invention relates to the manufacture of compounds comprising nitrile functional groups and of cyclic imide compounds.

It relates more particularly to the manufacture of compounds comprising nitrile functional groups from compounds comprising carboxyl functional groups, advantageously of natural and renewable origin, and from a mixture N of dinitriles comprising 2-methylglutaronitrile (MGN), 2-ethylsuccinonitrile (ESN) and adiponitrile (AdN).

Compounds comprising nitrile functional groups are important products for the manufacture of amine compounds. Dinitrile compounds result in amines which are, for example, monomers which are the source of polymers, such as polyamide, for example. Mononitrile compounds result in amines or in amides which are, for example, used for the manufacture of cationic surfactants.

Many processes for the synthesis of nitriles have been provided, in particular synthesis processes starting from ammonia and from carboxylic acids. These processes mainly use, as starting raw material, hydrocarbon compounds resulting from oil refining, and ammonia, which is obtained from hydrogen originating from steam reforming processes, which consume gas and energy.

Given that oil resources are running out, many research studies are being undertaken in order to develop processes for the synthesis of these compounds, which are important in the manufacture of materials used in numerous applications, from raw materials or resources termed renewable, or from recycled raw materials, which are normally destroyed or given added value only in the form of energy. Generally, these renewable resources are produced from cultivated or non-cultivated vegetable matter, such as trees, plants, for example sugarcane, corn, cassava, wheat, rape, sunflower, palm, castor oil plant or the like, or from animal matter, such as fats (tallow, and the like).

This vegetable or animal matter is converted by processes generally comprising several mechanical, chemical, indeed even biological, stages.

Moreover, with regard to the recycled raw materials, the manufacture of adiponitrile, a major chemical intermediate used in particular in the synthesis of hexamethylenediamine and caprolactam (monomers for the manufacture of polyamides), obtained by hydrocyanation of butadiene, generates a stream of dinitrile by-products predominantly comprising branched dinitrile compounds, such as 2-methylglutaronitrile or 2-ethylsuccinonitrile. This mixture of branched dinitrile compounds is obtained by distillation in order to separate it from the adiponitrile. As the separation is not generally complete, the mixture of branched dinitrile compounds can also comprise a small proportion of adiponitrile.

Several solutions have been provided for giving added value to these by-products or mixtures. One of these consists in hydrogenating the dinitrile compounds to give primary amines, in particular for producing 2-methylpentamethylenediamine (MPMD), used as monomer in the manufacture of specific polyamides or as intermediate in the production of vitamin B3 (nicotinamide). This process requires stages of purification of the 2-methylglutaronitrile and the 2-methylpentamethylenediamine.

Industrially, these by-products are also made use of economically in the form of vapor or energy by combustion. However, this combustion can require treatment of the gases in order to remove the nitrogen oxides produced and it produces carbon dioxide gas which is discharged to the atmosphere.

There thus exists a considerable demand and need to find new routes for giving added value to and converting these dinitrile compounds or mixtures into chemical compounds which can be given added value and which are economically advantageous.

To this end, the invention provides a process for the preparation of at least one nitrile of general formula I

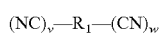

or respectively of at least one nitrile of general formula III

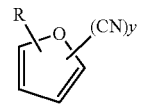

or respectively of at least one nitrile of general formula V

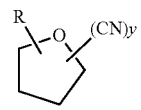

and of at least the cyclic imide 3-methylglutarimide,
by reaction between at least one carboxylic acid of general formula II

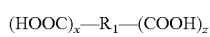

or respectively at least one carboxylic acid of general formula IV

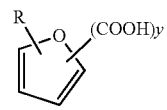

or respectively at least one carboxylic acid of general formula VI

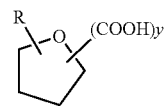

and at least 2-methylglutaronitrile (MGN), in the presence of a Lewis acid catalyst, with
x, z is equal to 0 or 1 with (x+z) equal to 1 or 2,
v, w is equal to 0 or 1 with (v+w) equal to 1 or 2,
$R_1$ represents a saturated or unsaturated and linear or branched hydrocarbon group which can comprise heteroatoms, comprising:

from 4 to 34 carbon atoms when (x+z) is equal to 2,
from 2 to 22 carbon atoms when (x+z) is equal to 1,
y is equal to 1 or 2,
R symbolizes one or more substituents.

The carboxylic acid of formula IV or VI can carry one or more substituents.

Advantageously, a mixture N of dinitriles comprising 2-methylglutaronitrile (MGN), 2-ethylsuccinonitrile (ESN) and adiponitrile (AdN) is employed. At least the cyclic imides 3-methylglutarimide and 3-ethylsuccinimide are then obtained.

Preferably, the mixture N of dinitriles is a mixture resulting from the process for the manufacture of adiponitrile by double hydrocyanation of butadiene. It preferably corresponds to the distillation fraction which makes it possible to separate the branched dinitriles (2-methylglutaronitrile, 2-ethylsuccinonitrile) from adiponitrile.

This mixture of dinitriles generally has the following composition by weight:
2-Methylglutaronitrile: between 70% and 95%, preferably between 80% and 85%,
2-Ethylsuccinonitrile: between 5% and 30%, preferably between 8% and 12%,
Adiponitrile: between 0% and 10%, preferably between 1% and 5%,
the remainder to 100% corresponding to various impurities.

The process of the invention uses a carboxylic acid of general formula II, IV or VI as described above.

Advantageously, the carboxylic acid of general formula II, IV or VI results from a renewable material of vegetable or animal origin.

A renewable material or resource is a natural, animal or plant, resource, the stock of which can be reconstituted over a short period on the human timescale. It is in particular necessary for this stock to be able to be renewed as quickly as it is consumed.

Unlike materials resulting from fossil materials, renewable raw materials contain a high proportion of $^{14}C$. Preferably, the nitriles of the invention consist of organic carbon resulting from renewable raw materials. Thus, this preferred characteristic might be certified by determining the $^{14}C$ content according to one of the methods described in the standard ASTM D6866, in particular according to the mass spectrometry method or the liquid scintillation spectrometry method which are described in this standard.

These renewable resources can be produced from cultivated or non-cultivated vegetable matter, such as trees, plants, for example sugarcane, corn, cassava, wheat, rape, sunflower, palm, castor oil plant or the like, or from animal matter, such as fats (tallow, and the like).

For example, the carboxylic acid of general formula II, IV or VI can result from renewable resources, such as vegetable oils or natural polysaccharides, such as, for example, starch or cellulose, it being possible for the starch to be extracted, for example, from corn, wheat or potato. It can in particular originate from various conversion processes, in particular conventional chemical processes, enzymatic conversion processes or fermentation conversion processes.

When the compound of formula II is a fatty monoacid, the latter can, for example, be obtained from vegetable or animal oil by chemical conversion (hydrolysis of the oils).

When the compound of formula II is a diacid, the latter can be obtained by fermentation from a fatty monoacid obtained according to the above method. For example, it is possible to use the yeast *Candida tropicalis* modified in order to carry out the conversion of a monoacid to a diacid. Reference may in particular be made to the documents WO 91/06660 and U.S. Pat. No. 4,474,882. The diacid can also be obtained from vegetable or animal oil by chemical conversion.

When the starting material is a polysaccharide, the compound of formula II is generally obtained by fermentation.

2,5-Furandicarboxylic acid can, for example, be obtained from mucic acid or from hydroxymethylfurfural.

The $R_1$ radical can be an aliphatic radical, a group comprising an aromatic or cycloaliphatic radical, it can be functionalized, for example by a hydroxyl functional group, an ester functional group, and the like.

The compound of formula II can, for example, be chosen from trichloroacetic acid, trifluoroacetic acid, caproic acid, caprylic acid, pelargonic acid, capric acid, lauric acid, myristic acid, palmitic acid, stearic acid, arachidic acid, adipic acid, heptanedioic acid, octanedioic acid, azelaic acid, sebacic or undecanedioic acid, dodecanedioic acid, brassylic acid, tetradecanedioic acid, hexadecanedioic acid, octadecanedioic acid, eicosanedioic acid, docosanedioic acid, octadecenoic acid, oleic acid, ricinoleic acid, erucic acid, linoleic acid, linolenic acid and fatty acid dimers comprising 36 carbon atoms, terephthalic acid or isophthalic acid.

Advantageously, the compound of formula II is chosen from caproic acid, caprylic acid, pelargonic acid, capric acid, lauric acid, myristic acid, palmitic acid, stearic acid, arachidic acid, adipic acid, heptanedioic acid, octanedioic acid, azelaic acid, sebacic or undecanedioic acid, dodecanedioic acid, brassylic acid, tetradecanedioic acid, hexadecanedioic acid, octadecanedioic acid, eicosanedioic acid, docosanedioic acid, octadecenoic acid, oleic acid, ricinoleic acid, erucic acid, linoleic acid, linolenic acid and fatty acid dimers comprising 36 carbon atoms, terephthalic acid or isophthalic acid.

Azelaic acid can be obtained from oleic acid by ozonolysis.

Heptanedioic acid and sebacic acid can be obtained from castor oil.

Dodecanedioic acid can be obtained by biofermentation of dodecanoic acid, also known as lauric acid, it being possible for the lauric acid to be produced from coconut oil or palm kernel oil.

Brassylic acid can be obtained from erucic acid (in particular by ozonolysis), it being specified that erucic acid occurs in the ester form in rape.

Tetradecanedioic acid can be obtained by biofermentation of myristic acid, it being possible for the myristic acid to be produced from coconut oil or palm kernel oil.

Hexadecanedioic acid can be obtained by biofermentation of palmitic acid, the latter occurring mainly in palm oil.

Octadecanedioic acid can be obtained by biofermentation of stearic acid, it being specified that the stearic acid can be present in all vegetable oils but in particular in animal fat.

Eicosanedioic acid can be obtained by biofermentation of arachidic acid, which is found predominantly in rapeseed oil.

Docosanedioic acid can be obtained by metathesis of undecylenic acid, which is extracted from castor oil.

The linear aliphatic diacid having 36 carbon atoms is a fatty acid dimer resulting, for example, from the by-products of the coniferous trees converted by Kraft processes. It can also be obtained by oligomerization or polymerization of unsaturated monobasic long-chain hydrocarbon fatty acids (such as linoleic acid and oleic acid), as described in particular in the document EP 0 471 566.

Advantageously, R is chosen from:
linear or branched alkyl groups preferably having from 1 to 6 carbon atoms and more preferentially still from 1 to 4 carbon atoms,
linear or branched mono-, poly- or perhalogenated alkyl groups preferably having from 1 to 6 carbon atoms and from 1 to 13 halogen atoms and more preferably still from 1 to 4 carbon atoms and from 1 to 9 halogen atoms, ether $R_2$—O— or thioether $R_2$—S— groups in which $R_2$ represents a linear or branched alkyl group having from 1 to 6 carbon atoms and more preferably still from 1 to 4 carbon atoms or the phenyl group, acyloxy or aroyloxy $R_2$—CO—O— groups in which the $R_2$ group has the meanings given above, acyl or aroyl $R_2$—CO— groups in which the $R_2$ group has the meanings given above, the hydroxyl group, a halogen atom, preferably a fluorine atom.

According to a specific embodiment of the invention, y is equal to 1 and R represents —CO—O—$R_3$ with $R_3$ which represents an alkyl group having from 1 to 4 carbon atoms in the general formula IV or VI.

Preferably, the compound of formula IV or VI is chosen from 2,5-furandicarboxylic acid, 2,5-tetrahydrofurandicarboxylic acid, 2-furoic acid, 2,5-furandicarboxylic acid monomethyl ester or 2,5-tetrahydrofurandicarboxylic acid monomethyl esters.

In the context of the process of the invention, use may be made of a mixture of several carboxylic acids, for example a carboxylic acid of general formula II or IV or VI and another carboxylic acid, or a mixture of several carboxylic acids of formula II (or IV or VI). Mention may be made, as example of mixture of acids, of coco acids, which result from palm oil or coconut oil, tallow acids, and the like.

The reaction of the invention is carried out in the presence of a Lewis acid catalyst. Mention may be made, as example of Lewis acid, of $AlCl_3$, $FeCl_3$, $ZnCl_2$, $TiCl_4$ or lanthanide triflates, such as $Yb(OTf)_3$.

The amount of catalyst employed is advantageously between 0.1 mol % and 4 mol %, preferably between 0.5 mol % and 2 mol %, with respect to the number of moles of reactants employed.

The reaction medium can comprise traces of water.

The process of the invention is advantageously carried out at a temperature of between 150 and 350° C. The pressure used is generally between atmospheric pressure and a few bar.

The process of the invention can also be carried out by application of microwaves to the reaction mixture, as an alternative to conventional heating. The irradiation times are advantageously between 10 and 30 minutes, preferably between 5 and 15 minutes.

Advantageously, an amount of 2-methylglutaronitrile (MGN) or of mixture N is used such that at least one molecule of 2-methylglutaronitrile (MGN) or of 2-ethylsuccinonitrile (ESN) is introduced into the reaction medium, per acid functional group of the carboxylic acid of general formula II or IV or VI to be converted into nitrile functional group.

When a diacid is used as acid of general formula II or IV or VI, it is possible to obtain the corresponding dinitrile or the corresponding acid nitrile (for example, by using a deficiency of nitrile functional group).

During the reaction between the compound of formula (II) or (IV) or (VI) and the mixture N of dinitriles in accordance with the invention, imides are formed, in particular 3-methylglutarimide, resulting from MGN, and 3-ethylsuccinimide, resulting from ESN.

Advantageously, the process of the invention also comprises a stage of recovery, on the one hand, of at least the nitrile of formula (I) or (III) or (V) and, on the other hand, of at least the cyclic imide, from the reaction medium.

This recovery can be carried out by separation of the compounds of the reaction medium, according to any known method, such as distillation.

According to a first advantageous embodiment, the compounds can be obtained by reactive distillation. This is because, when the nitrile of formula (I) or (III) or (V) which it is desired to obtain has a boiling point below that of the reaction temperature (which is in particular the case for nitriles having a low carbon number), this nitrile can be distilled as it is formed, thereby shifting the equilibrium of the reaction toward the formation of this nitrile; this is therefore particularly advantageous. This reactive distillation method can, for example, be used when the nitrile of formula (I) or (III) or (V) is 2,5-dicyanotetrahydrofuran or a mononitrile, such as octanitrile or nonanitrile.

According to a second advantageous embodiment, the compounds can be separated by extraction with hot water. This is because imides are generally soluble in water, unlike in particular nitriles, which allows good separation via a route which is easy to implement. This route is to be favored in particular when the nitriles and the imides to be separated have boiling points which are close and when they are consequently difficult to separate by conventional distillation, for example. This method of extraction with hot water can, for example, be used when the nitrile of formula (I) is lauronitrile or oleonitrile or when a mixture of acids of formula (II) is employed. The temperature of the water during this extraction is generally greater than or equal to 50° C.

According to a specific embodiment of the invention, the nitrile of formula (I) or (III) or (V) thus recovered is hydrogenated in order to form the corresponding amine, according to a method known to a person skilled in the art. When a nitrile of formula (III) is recovered, its hydrogenation can result in the amine corresponding to the compound of formula (V), by hydrogenation not only of the nitrile functional group but also by hydrogenation of the double bonds of the furan ring. An amine is thus obtained, all the carbons of which are bio-based (as resulting from a bio-based carboxylic acid, that is to say a carboxylic acid resulting from a renewable raw material) and the nitrogen atoms of which are recycled (as resulting from by-products which are usually incinerated, thereby generating carbon dioxide and nitrogen oxides, which are greenhouse gases which must be treated in order to meet the legislation in force). The diamines can be used as raw materials for the manufacture of polyamides, which will thus be partially or completely bio-based, depending on the acids used for the polymerization. The amines can also be used to prepare surfactants.

According to another specific embodiment of the invention, the cyclic imide recovered according to the process of the invention can be reacted with an alcohol in order to form the corresponding diester. Such a process is known and in particular described in the documents WO 2008/009792 and WO 2009/056477. The diesters can be used as solvents.

Other details or advantages of the invention will become more clearly apparent in the light of the examples given below.

EXAMPLES

In the examples, the following reaction is carried out:

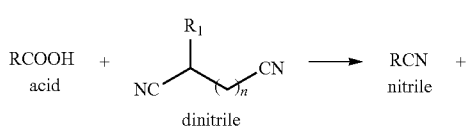

-continued

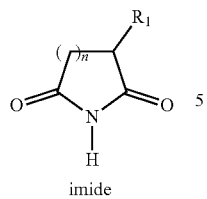

imide with n=2,
$R_1$=H or $CH_3$.

The operating conditions of the examples and also the results are shown in the table below.

Compound 1 in the table is as follows:

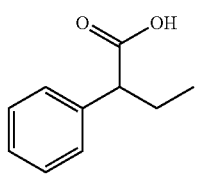

The molar percentage of catalyst in the table is expressed with respect to the molar sum of the acid and dinitrile reactants.

TABLE

| Examples | Acid | Dinitrile | Catalyst mol % | Procedure | DC % acid | RY % nitrile | RY % imide |
|---|---|---|---|---|---|---|---|
| 1, comp. | Compound 1 | glutaronitrile | — | thermal | 44 | 40 | 42 |
| 1 | Compound 1 | glutaronitrile | AlCl₃ 2% | thermal | 85 | 83 | 84 |
| 2 | Compound 1 | glutaronitrile | Yb(OTf)₃ 1% | thermal | 90 | 69 | 85 |
| 3 | Compound 1 | glutaronitrile | ZnCl₂ 1% | thermal | 68 | 66 | 67 |
| 2, comp. | Compound 1 | glutaronitrile | — | micro-waves | 74 | 62 | 68 |
| 4 | Compound 1 | glutaronitrile | AlCl₃ 1% | micro-waves | 85 | 75 | 80 |
| 5 | Compound 1 | glutaronitrile | ZnCl₂ 1% | micro-waves | 86 | 86 | 86 |
| 6 | Compound 1 | 2-methyl-glutaronitrile | AlCl₃ 1% | thermal | 84 | 76 | 83 |
| 7 | 3,4,5-trimethoxybenzoic acid | glutaronitrile | AlCl₃ 1% | micro-waves | 83 | 83 | 83 |
| 8 | 3,4,5-trimethoxybenzoic acid | glutaronitrile | AlCl₃ 1% | micro-waves | 57 | 52 | 55 |
| 9 | 3,3-diphenylpropanoic acid | glutaronitrile | AlCl₃ 1% | micro-waves | 84 | 80 | 82 |
| 10 | 3-methoxycinnamic acid | glutaronitrile | AlCl₃ 1% | micro-waves | 66 | 40 | 65 |

The two procedures, thermal and microwaves, shown in the table are described below.

Thermal Procedure:

The dinitrile (3.0 mmol, 1.0 equiv.) is added, in a glass tube, to a mixture of acid (3.0 mmol) and catalyst (0.06 mmol, 0.02 equiv., except for example 1, where 0.12 mmol, 0.04 equiv., is employed). The tube is then hermetically closed (using a screw stopper) and left mechanically stirring at 200° C. for 5 h. After reaction, the crude reaction mixture is transferred into a 50 ml round-bottomed flask with 10 ml of ethanol. If necessary, the tube is placed in an ultrasonic bath at 60° C., in order to promote the dissolution of the reaction mixture in the ethanol. 3 g of silica are subsequently added to this mixture in order to produce a solid deposit after evaporation of the ethanol. Finally, the pure nitrile is obtained after chromatography on a silica column (gradient from $M_1$ to $M_9$, followed by $M_0$). For its part, the cyclic imide is obtained after elution with ethyl acetate. The conversion to the desired nitrile is determined by $^1H$ NMR of the crude product. The yields shown are the yields of the isolated products after purification.

Microwaves Procedure:

The dinitrile (3.0 mmol, 1.0 equiv.) is added, in a glass tube designed for this purpose, to a mixture of acid (3.0 mmol) and catalyst (0.06 mmol, 0.02 equiv.). The tube is then closed using a suitable stopper and then is left under microwave activation (appliance used: Monowave® 300 from Anton Paar) and magnetic stirring at 300° C. for 10 min. After reaction, the crude reaction mixture is transferred into a 50 ml round-bottomed flask with 10 ml of ethanol. If necessary, the tube is placed in an ultrasonic bath at 60° C., in order to promote the dissolution of the reaction mixture in the ethanol. 3 g of silica are subsequently added to this mixture in order to produce a solid deposit after evaporation of the ethanol. Finally, the pure nitrile is obtained after chromatography on a silica column (gradient from $M_1$ to $M_9$, followed by $M_0$). For its part, the cyclic imide is obtained after elution with ethyl acetate. The conversion to the desired nitrile is determined by $^1H$ NMR of the crude product. The yields shown are the yields of the isolated products after purification.

Note:
- $M_0$ is an 80:20 dichloromethane/ethyl acetate mixture.
- $M_1$ is a 90:10 petroleum ether/$M_0$ mixture.
- $M_2$ is an 80:20 petroleum ether/$M_0$ mixture, and the like.
- $M_9$ is a 10:90 petroleum ether/$M_0$ mixture.

Example 6, Comparative 200 mmol of 2-methylglutaronitrile are introduced into a 100 ml three-necked flask and 200 mmol of 2-phenylbutanoic acid are added. Stirring is carried out and 4 mmol of 85% orthophosphoric acid are added to the suspension. The reaction medium is then heated at 200° C. for 5 hours. After this time, the reaction medium is analyzed and the following results are obtained:

DC % of the MGN=52%, RY % for MGI=51%, RY % for 2-phenylbutanenitrile=45%.

Example 11

200 mmol of 2-methylglutaronitrile and 100 mmol of dodecanedioic acid are introduced into a 100 ml three-necked flask. 3 mmol of anhydrous $AlCl_3$ are added to the suspension. Heating to 200° C. is then carried out with stirring. The mixture is maintained under these conditions for 5 hours. The reaction medium is subsequently analyzed and the following results are obtained:

DC % of the MGN=90%, RY % of the MGI=88%, RY % for dodecanedinitrile=81%.

Example 12

130 g (1200 mmol) of 2-methylglutaronitrile and 20 g (120 mmol) of isophthalic acid are introduced into a 250 ml glass reactor. The white suspension is stirred and 0.32 g (2.4 mmol) of anhydrous aluminum chloride is added. The mixture is gradually heated to 270° C. and is maintained under these conditions for 4 h.

During the rise in temperature, the isophthalic acid dissolves in the MGN.

The reaction medium is subsequently analyzed by GC. An RY % for MGI of 76% and a yield of 1,3-dicyanobenzene of 69% are obtained.

The invention claimed is:

1. A process for the preparation of at least one nitrile of general formula I:

$$(NC)_v—R_1—(CN)_w \quad (I)$$

by reaction between at least one carboxylic acid of general formula II:

$$(HOOC)_x—R_1—(COOH)_z \quad (II)$$

and one or more dinitriles, comprising at least 2-methylglutaronitrile (MGN), in the presence of a Lewis acid catalyst, wherein:
- each of x, z is equal to 0 or 1 with (x+z) equal to 1 or 2,
- each of v, w is equal to 0 or 1 with (v+w) equal to 1 or 2,
- $R_1$ represents a saturated or unsaturated and linear or branched hydrocarbon group which can comprise heteroatoms, comprising:
  - from 4 to 34 carbon atoms when (x+z) is equal to 2, and
  - from 2 to 22 carbon atoms when (x+z) is equal to 1.

2. The process as claimed in claim 1, wherein a mixture N of dinitriles comprising 2-methylglutaronitrile (MGN), 2-ethylsuccinonitrile (ESN) and adiponitrile (AdN) is employed as a source of the one or more dinitriles.

3. The process as claimed in claim 1, wherein the mixture N of dinitriles is a mixture resulting from the process for the manufacture of adiponitrile by double hydrocyanation of butadiene.

4. The process as claimed in claim 2 wherein the mixture N of dinitriles has the following composition by weight:
- 2-Methylglutaronitrile: between 70% and 95%,
- 2-Ethylsuccinonitrile: between 5% and 30%,
- Adiponitrile: between 0% and 10%, and
- the remainder to 100% corresponding to various impurities.

5. The process as claimed in claim 1 wherein the compound of formula II results from a renewable material of vegetable or animal origin.

6. The process as claimed in claim 1, wherein the compound of formula II is chosen from caproic acid, caprylic acid, pelargonic acid, capric acid, lauric acid, myristic acid, palmitic acid, stearic acid, arachidic acid, adipic acid, heptanedioic acid, octanedioic acid, azelaic acid, sebacic or undecanedioic acid, dodecanedioic acid, brassylic acid, tetradecanedioic acid, hexadecanedioic acid, octadecanedioic acid, eicosanedioic acid, docosanedioic acid, octadecenoic acid, oleic acid, ricinoleic acid, erucic acid, linoleic acid, linolenic acid and fatty acid dimers comprising 36 carbon atoms, or terephthalic acid.

7. The process as claimed in claim 1, wherein the process further comprises a stage of recovery, on the one hand, of at least the nitrile and, on the other hand, of at least the cyclic imide 3-methylglutarimide, by separation of the compounds of the reaction medium.

8. The process as claimed in claim 7, wherein at least the recovered nitrile is hydrogenated in order to form the corresponding amine.

9. The process as claimed in claim 7 wherein at least the recovered cyclic imide 3-methylglutarimide is reacted with an alcohol in order to form the corresponding diester.

10. The process as claimed in claim 2, wherein the mixture N of dinitriles comprises:
- between 80% and 85% by weight of 2-methylglutaronitrile,
- between 8% and 12% by weight of 2-ethylsuccinonitrile, and
- between 1% and 5% by weight of adiponitrile.

\* \* \* \* \*